(12) United States Patent
Kishore et al.

(10) Patent No.: US 11,935,389 B2
(45) Date of Patent: Mar. 19, 2024

(54) METHODS AND APPARATUSES FOR MONITORING INTRAVENOUS FLUID BAGS

(71) Applicant: Honeywell International Inc., Charlotte, NC (US)

(72) Inventors: Kuna Venkat Satya Rama Kishore, Bangalore (IN); Gurudutt K K, Bangalore (IN); Praneesh Kumar Yadav Kataru, Bangalore (IN)

(73) Assignee: Honeywell International Inc., Charlotte, NC (US)

( * ) Notice: Subject to any disclaimer, the term of this patent is extended or adjusted under 35 U.S.C. 154(b) by 0 days.

(21) Appl. No.: 17/818,864

(22) Filed: Aug. 10, 2022

(65) Prior Publication Data

US 2024/0054884 A1 Feb. 15, 2024

(51) Int. Cl.
*G08B 25/14* (2006.01)
*G08B 25/10* (2006.01)
*G08B 25/00* (2006.01)

(52) U.S. Cl.
CPC ............. *G08B 25/14* (2013.01); *G08B 25/10* (2013.01); *G08B 25/008* (2013.01)

(58) Field of Classification Search
CPC ....... G08B 25/14; G08B 25/10; G08B 25/008
See application file for complete search history.

(56) References Cited

U.S. PATENT DOCUMENTS

| | | | | |
|---|---|---|---|---|
| 5,563,584 | A * | 10/1996 | Rader | A61M 5/1684 73/299 |
| 6,690,280 | B2 * | 2/2004 | Citrenbaum | G01G 17/04 128/DIG. 13 |
| 9,539,389 | B2 | 1/2017 | Trombly et al. | |
| 10,458,833 | B2 | 10/2019 | Rossi | |
| 2009/0069796 | A1 | 3/2009 | Oskin | |
| 2011/0166433 | A1 * | 7/2011 | Dalebout | A61B 5/150221 600/362 |
| 2012/0226446 | A1 | 9/2012 | Nelson et al. | |
| 2018/0296792 | A1 * | 10/2018 | Hochman | A61M 19/00 |
| 2019/0381233 | A1 * | 12/2019 | Frinak | A61M 5/16854 |

FOREIGN PATENT DOCUMENTS

| | | | | |
|---|---|---|---|---|
| CN | 104874036 B | * | 7/2019 | ............ A61M 1/34 |
| JP | 5330393 B2 | | 10/2013 | |
| WO | WO-2009108676 A2 | * | 9/2009 | ........... A61B 5/1411 |
| WO | WO-2015038632 A1 | * | 3/2015 | ........... A61M 39/08 |

OTHER PUBLICATIONS

Extended European Search Report dated Dec. 22, 2023 for EP Application No. 23184928, 7 page(s).

* cited by examiner

*Primary Examiner* — Naomi J Small
(74) *Attorney, Agent, or Firm* — Alston & Bird LLP

(57) ABSTRACT

Systems and methods for monitoring intravenous (IV) fluid bags are provided. The system includes a replaceable unit comprising a sensor comprising a pressure sensor configured to measure hydrostatic pressure, an electrical connector coupling the sensor to a controller component, a cannula configurable for insertion into a fluid port of an IV fluid bag, and an IV tube coupling the sensor to an IV fluid bag via the cannula. The system further includes the controller component configured to retrieve data representative of hydrostatic pressure from the sensor and calculate remaining fluid volume, discharge rate, and flow occlusion based on the retrieved data.

20 Claims, 9 Drawing Sheets

METHODS AND APPARATUSES FOR MONITORING INTRAVENOUS FLUID BAGS

FIELD OF THE INVENTION

Example embodiments of the present disclosure relate generally monitoring intravenous (IV) fluid bags, and more particularly, to methods, apparatuses, and systems for real-time monitoring of an IV fluid bag.

BACKGROUND

Administering an IV fluid (e.g., saline, dextrose, or any medication) as part of patient care in a hospital/clinic environment is common practice. A general protocol in administering IV fluid by intra-venous route may comprise an authorized nursing staff connect a patient to an IV fluid bag containing a prescribed fluid along with an IV tube set and set a required dosing. Afterwards, the nursing staff may monitor from time to time by examining, for example, a drip chamber, the IV fluid bag, the IV tube set, and an administration site to monitor correct dosing, fluid level in the IV fluid bag, and kinks or twisting. Any deviations from the norm may be corrected by nursing staff. However, in typical scenarios when attending general wards, nursing staff is overwhelmed with many repetitive patient visits and may result in service deficiency.

BRIEF SUMMARY

Various embodiments described herein relate to components, apparatuses, and systems for monitoring IV fluid bags.

In accordance with various embodiments of the present disclosure, an IV fluid bag monitoring system is provided. In some embodiments, the IV fluid bag monitoring system may comprise a replaceable unit comprising a sensor comprising a pressure sensor configured to measure hydrostatic pressure, an electrical connector coupling the sensor to a controller component, a cannula configurable for insertion into a fluid port of an IV fluid bag, and an IV tube coupling the sensor to an IV fluid bag via the cannula. In some embodiments, the controller component may be configured to retrieve data representative of hydrostatic pressure from the sensor, and calculate remaining fluid volume, discharge rate, and flow occlusion based on the retrieved data.

In some embodiments, the controller component may be further configured to transmit data load packages to a remote computing server, the data load packages including the retrieved data and the calculated remaining fluid volume, discharge rate, and flow occlusion. In some embodiments, the controller component may further include visual and acoustic indicators that show respective alert and alarms with respect to the calculated remaining fluid, discharge rate, and flow occlusion. In some embodiments, the controller component may be configured on a stand at a height that is level with the fluid port. In some embodiments, the sensor may be configured to measure hydrostatic pressure of fluid transmitted through the IV tube from the IV fluid bag at the fluid port. In some embodiments, the controller component may be further configured to store at least values for an initial pressure and a current pressure, and calculate remaining fluid volume based on the current pressure and the initial pressure. In some embodiments, the controller component may be further configured to determine the remaining fluid volume is below a given threshold, and generate an alert or alarm based on the remaining fluid volume being below the given threshold.

In some embodiments, the controller component may be further configured to calculate average pressure change rate based on pressure data reading values over a plurality of time blocks, for each of the plurality of time blocks, store an average pressure change rate as an instance, and calculate average discharge rate deviation based on average pressure change rate over a plurality of stored instances. In some embodiments, the controller component may be further configured to generate flow discharge alerts and alarms based on a difference between an average discharge rate deviation of a prior instance and an average discharge rate deviation of a current instance being greater than or less than a threshold value of the average discharge rate deviation of the prior instance. In some embodiments, the controller component may be further configured to: count a number of successive flow occlusion events. In some embodiments, the flow occlusion events may include a decrease in average discharge rate deviation below a given threshold. In some embodiments, the controller component may be further configured to: determine whether a difference between an average discharge rate deviation of a prior instance and an average discharge rate deviation of a current instance is less than 1% of the average discharge rate deviation of the current instance. In some embodiments, the controller component may be further configured to: determine the number of successive flow occlusion events is greater than an occlusion counter flag.

According to another embodiment, IV fluid bag monitoring system comprises a sensor comprising a pressure sensor configured to measure hydrostatic pressure, a replaceable unit comprising a cannula configurable for insertion into a fluid port of an IV fluid bag, an IV tube coupling the sensor to an IV fluid bag via the cannula, and a fluid connector coupling the IV tube to the sensor. The IV fluid bag monitoring system may further comprise an electrical connector coupling the sensor to a controller component, and the controller component configured to retrieve data representative of hydrostatic pressure from the sensor, and calculate remaining fluid volume, discharge rate, and flow occlusion based on the retrieved data.

In some embodiments, the sensor may be configured to measure hydrostatic pressure of fluid transmitted through the IV tube from the IV fluid bag at the fluid port. In some embodiments, the controller component may be further configured to store at least values for an initial pressure and a current pressure, and calculate remaining fluid volume based on the current pressure and the initial pressure. In some embodiments, the controller component may be further configured to determine the remaining fluid volume is below a given threshold, and generate an alert or alarm based on the remaining fluid volume being below the given threshold. In some embodiments, the controller component may be further configured to calculate average pressure change rate based on pressure data reading values over a plurality of time blocks, store an average pressure change rate as an instance, and calculate average discharge rate deviation based on average pressure change rate over a plurality of stored instances. In some embodiments, the controller component may be further configured to generate flow discharge alerts and alarms based on a difference between an average discharge rate deviation of a prior instance and an average discharge rate deviation of a current instance being greater than or less than a threshold value of the average discharge rate deviation of the prior instance. In some embodiments, the controller component may be further configured to count a number of successive flow occlusion events.

The foregoing illustrative summary, as well as other exemplary objectives and/or advantages of the disclosure, and the manner in which the same are accomplished, are further explained in the following detailed description and its accompanying drawings.

BRIEF DESCRIPTION OF THE DRAWINGS

The description of the illustrative embodiments may be read in conjunction with the accompanying figures. It will be appreciated that, for simplicity and clarity of illustration, elements illustrated in the figures have not necessarily been drawn to scale, unless described otherwise. For example, the dimensions of some of the elements may be exaggerated relative to other elements, unless described otherwise. Embodiments incorporating teachings of the present disclosure are shown and described with respect to the figures presented herein, in which.

DETAILED DESCRIPTION OF THE INVENTION

Figure 1:
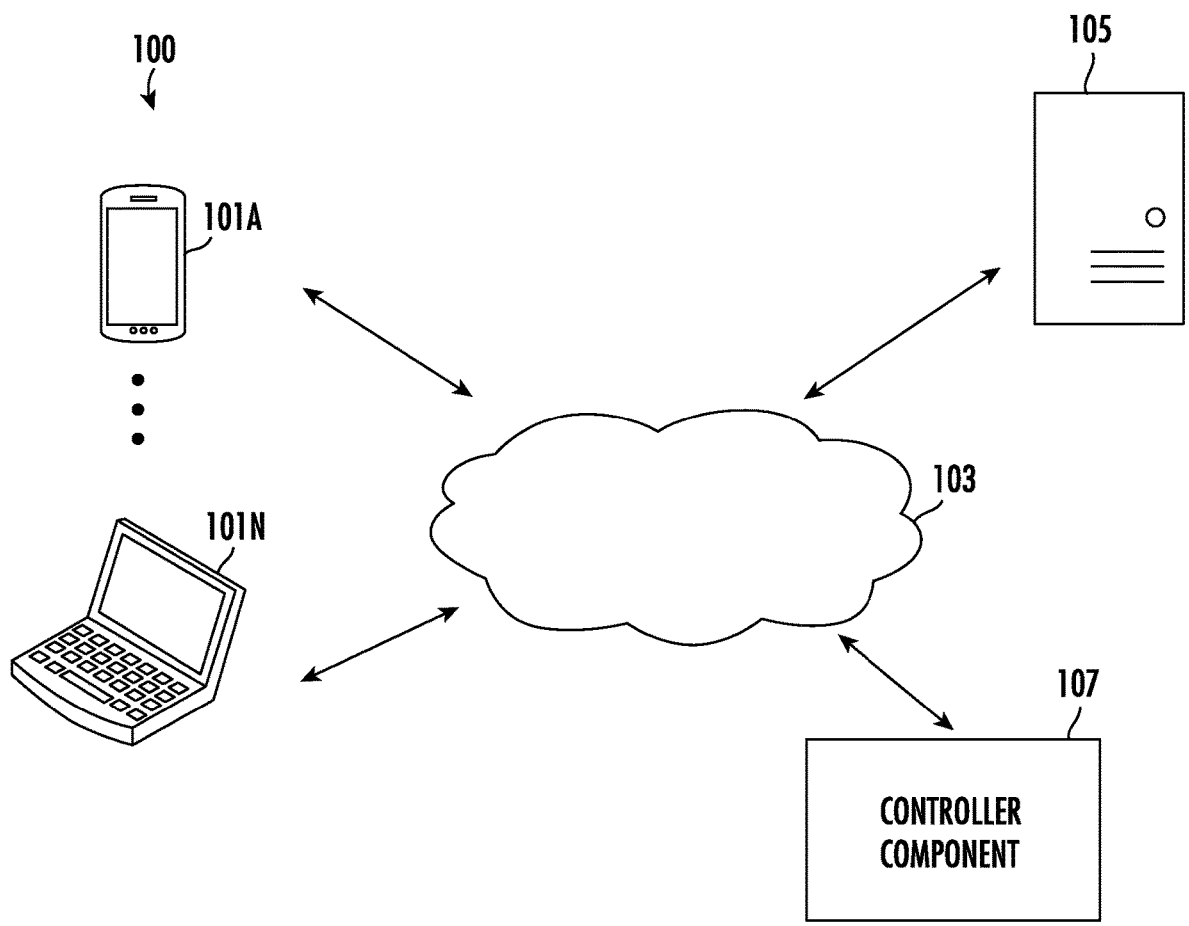
FIG. 1 illustrates an example analytics and monitoring system in accordance with various embodiments of the present disclosure.

Some embodiments of the present disclosure will now be described more fully hereinafter with reference to the accompanying drawings, in which some, but not all embodiments of the disclosure are shown. Indeed, these disclosures may be embodied in many different forms and should not be construed as limited to the embodiments set forth herein; rather, these embodiments are provided so that this disclosure will satisfy applicable legal requirements. Like numbers refer to like elements throughout.

As used herein, terms such as "front," "rear," "top," etc. are used for explanatory purposes in the examples provided below to describe the relative position of certain components or portions of components. Furthermore, as would be evident to one of ordinary skill in the art in light of the present disclosure, the terms "substantially" and "approximately" indicate that the referenced element or associated description is accurate to within applicable engineering tolerances.

As used herein, the term "comprising" means including but not limited to and should be interpreted in the manner it is typically used in the patent context. Use of broader terms such as comprises, includes, and having should be understood to provide support for narrower terms such as consisting of, consisting essentially of, and comprised substantially of.

The phrases "in one embodiment," "according to one embodiment," and the like generally mean that the particular feature, structure, or characteristic following the phrase may be included in at least one embodiment of the present disclosure, and may be included in more than one embodiment of the present disclosure (importantly, such phrases do not necessarily refer to the same embodiment).

The word "example" or "exemplary" is used herein to mean "serving as an example, instance, or illustration." Any implementation described herein as "exemplary" is not necessarily to be construed as preferred or advantageous over other implementations.

If the specification states a component or feature "may," "can," "could," "should," "would," "preferably," "possibly," "typically," "optionally," "for example," "often," or "might" (or other such language) be included or have a characteristic, that a specific component or feature is not required to be included or to have the characteristic. Such a component or feature may be optionally included in some embodiments, or it may be excluded.

Electronic real-time health monitoring systems ("RTHMS") may be deployed to assist healthcare staff, such as nurses, and hospital operations. RTHMS may typically assist in providing "virtual care" by collecting certain patient vitals for continuous monitoring and coordinated care. A RTHMS may include a communication platform for remote and real-time monitoring of patients. For example, a RTHMS may be coupled to sensing hardware to capture vital parameters of patients in real-time and transmits data corresponding to the vital parameters to, for example, a cloud computing network. The cloud computing network may perform analytics and monitoring of the data. Users of the RTHMS may retrieve, using client devices, the analytics and monitoring for rendering on, for example, a health analytics dashboard user interface on the client devices. The RTHMS may also generate alerts to the client devices in real-time based on any deviation in patients' vital signs against acceptable or normal ranges according to the analytics and monitoring.

Various example embodiments of the present disclosure provide various technical advancements and improvements to RTHMS. In accordance with various examples of the present disclosure, integration of an IV fluid bag monitoring system with RTHMS is disclosed. The disclosed IV fluid bag monitoring system may receive sensor data associated with IV fluid bags, process the data to determine IV fluid bag characteristics, such as fluid level, discharge rate and possible occlusion at patient side, and transmit the IV fluid bag characteristics to the RTHMS. The disclosed IV fluid bag monitoring system may also be integrated with nurse call systems to improve nursing staff productivity.

According to some embodiments, an IV fluid bag monitoring system may be configured to monitor IV fluid bags for remaining fluid volume, fluid discharge rate, and flow occlusion while being administered. The IV fluid bag monitoring system may include a controller component capable of executing program code to derive total remaining fluid volume, liquid discharge rate, and flow occlusion from measured hydrostatic pressure between a sensor height and an IV fluid bag fluid height. In some embodiments, the controller component may execute program code to derive percentage remaining fluid volume from temporal variation of hydrostatic pressure after setting an initial point, without requiring actual fluid bag volume information, such that this derivation is independent of IV fluid bag actual volume. In some embodiments, the controller component may execute program code to derive flow discharge rate as a percentage change in time to identify high and low flow discharge rate alarms/alerts without actual measure of flow rate, e.g., in milliliters/minute. In some embodiments, the controller component may execute program code to identify flow occlusion by determining change of hydrostatic pressure stagnation in time and comparing prevailing states with current state, without requiring actual measure of flow rate reduction.

The disclosed IV fluid bag monitoring system may also be provided as a frontend device for a RTHMS to improve nursing staff productivity with high/low alerts and alarms via visual and acoustic indications on the sensor apparatus. The controller component of the IV fluid bag monitoring system may determine IV fluid bag characteristics (e.g., total remaining fluid volume, liquid discharge rate, and flow occlusion) and transmit a data load package including the IV fluid bag characteristics for high/low alerts and alarms to a RTHMS. Data load packages may be transmitted to RTHMS periodically or upon calculation of IV fluid bag characteristics.

Referring now to FIG. 1, an example diagram illustrating an example analytics and monitoring system 100 in accordance with some example embodiments described herein is provided. As shown in FIG. 1, the example analytics and monitoring system 100 comprises apparatuses, devices, and components such as, but not limited to, a controller component 107, one or more client computing devices 101A . . . 101N, a remote computing server 105 in a remote computing platform, and one or more networks 103.

In some embodiments, each of the components of the example analytics and monitoring system 100 may be in electronic communication with, for example, one another over the same or different wireless or wired networks 103 including, for example, a wired or wireless Personal Area Network (PAN), Local Area Network (LAN), Metropolitan Area Network (MAN), Wide Area Network (WAN), and/or the like. Additionally, while FIG. 1 illustrates certain system entities as separate, standalone entities, the various embodiments are not limited to this particular architecture.

For example, the controller component 107, one or more client computing devices 101A . . . 101N, and the remote computing server 105 in the remote computing platform may be in electronic communication with one another to exchange data and information. As described herein, the controller component 107 may receive data from one or more sensors coupled to one or more IV fluid bags. In some embodiments, the controller component 107 may transmit data from the one or more sensors to the one or more client computing devices 101A . . . 101N and/or the remote computing server 105 in the remote computing platform for analysis. Data from the one or more sensors may be distributed into individual monitoring channels corresponding to each of the sensors.

In some embodiments, the one or more client computing devices 101A . . . 101N and/or the remote computing server 105 in the remote computing platform may receive the data from the controller component 107 and may generate estimated characteristics data associated with the one or more sensors coupled to one or more IV fluid bags based at least in part on the data. Examples of estimated characteristics data may include, but not limited to, remaining fluid volume, discharge rate, and flow occlusion. For example, the controller component 107 may transmit data to the one or more client computing devices 101A . . . 101N and/or the remote computing server 105. Upon receiving the data, the one or more client computing devices 101A . . . 101N and/or the remote computing server 105 may process the estimated characteristics data for rendering on a graphical user interface ("GUI"). In some embodiments, the one or more client computing devices 101A . . . 101N and/or the remote computing server 105 may generate one or more data points on the GUI based on the data in accordance with various example methods described herein, including, but not limited to, those described in connection with at least FIG. 7, FIG. 8, and FIG. 9.

Figure 2:
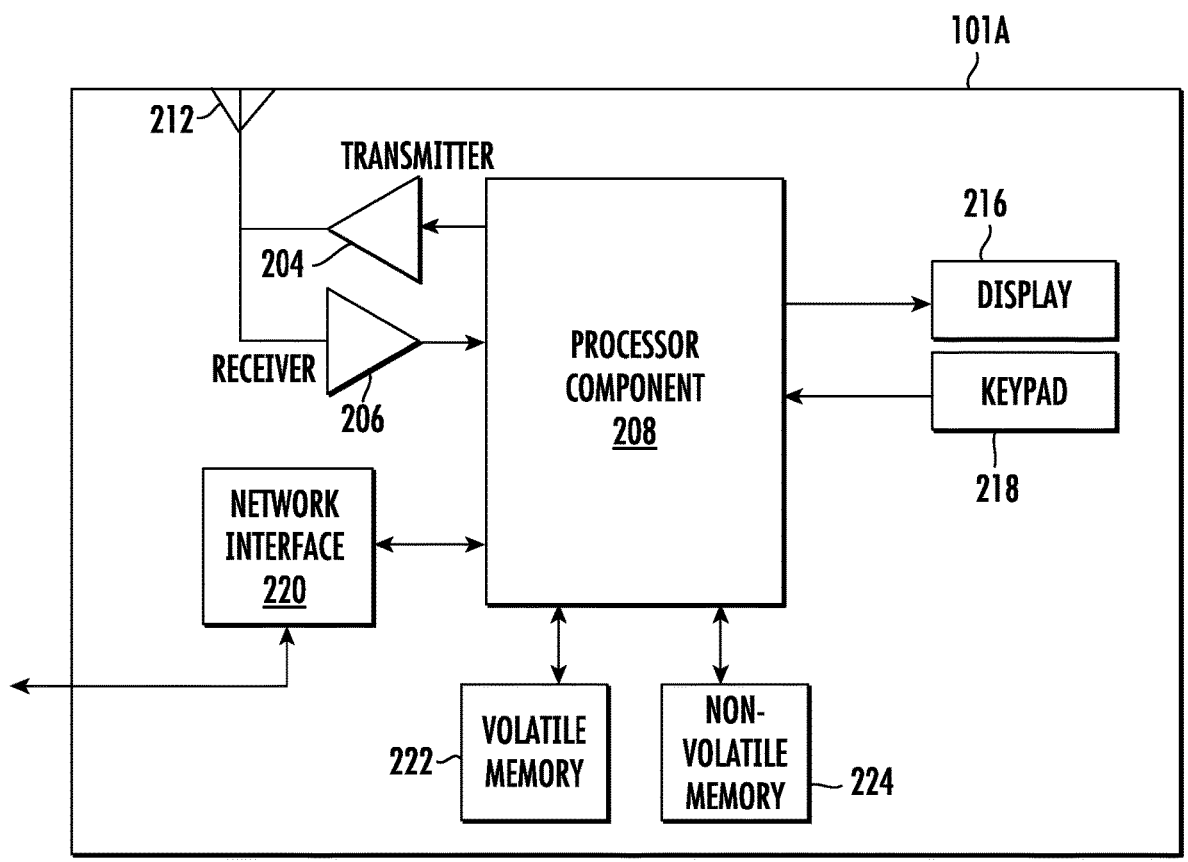
FIG. 2 illustrates an example schematic representation of an example client computing device in accordance with various embodiments of the present disclosure.

Referring now to FIG. 2, an example schematic representation of an example client computing device in accordance with some example embodiments described herein is provided. For example, FIG. 2 provides an illustrative schematic representative of one of the client computing devices 101A to 101N that can be used in conjunction with embodiments of the present disclosure. In some embodiments, as illustrated in FIG. 2, the client computing device 101A includes an antenna 212, a transmitter 204 (e.g., radio), a receiver 206 (e.g., radio), and a processor component 208 that provides signals to and receives signals from the transmitter 204 and receiver 206, respectively. The signals provided to and received from the transmitter 204 and the receiver 206, respectively, may include signaling information/data in accordance with an air interface standard of applicable wireless systems to communicate with various entities, such as a remote computing server 105, another client computing device 101A, an example monitoring system and/or the like. In this regard, the client computing device 101A may be capable of operating with one or more air interface standards, communication protocols, modulation types, and access types. More particularly, the client computing device 101A may comprise a network interface 220, and may operate in accordance with any of a number of wireless communication standards and protocols. In a particular embodiment, the client computing device 101A may operate in accordance with multiple wireless communication standards and protocols, such as GPRS, UMTS, CDMA1900, 1xRTT, WCDMA, TD-SCDMA, LTE, E-UTRAN, EVDO, HSPA, HSDPA, Wi-Fi, WiMAX, UWB, IR protocols, Bluetooth protocols, USB protocols, and/or any other wireless protocol.

Via these communication standards and protocols, the client computing device 101A can communicate with various other entities using Unstructured Supplementary Service data (USSD), Short Message Service (SMS), Multimedia Messaging Service (MMS), Dual-Tone Multi-Frequency (DTMF) Signaling, Subscriber Identity Module Dialer (SIM dialer), and/or the like. The client computing device 101A can also download changes, add-ons, and updates, for instance, to its firmware, software (e.g., including executable instructions, applications, program modules), and operating system.

The client computing device 101A may also comprise a user interface comprising one or more user input/output interfaces (e.g., a display 216 and/or speaker/speaker driver coupled to a processor component 208 and a touch screen, keyboard, mouse, and/or microphone coupled to a processor component 208). For example, the user output interface may be configured to provide an application, browser, user interface, dashboard, webpage, and/or similar words used herein interchangeably executing on and/or accessible via the client computing device 101A to cause display or audible presentation of information/data and for user interaction therewith via one or more user input interfaces. The user output interface may be updated dynamically from communication with the remote computing server 105. The user input interface can comprise any of a number of devices allowing the client computing device 101A to receive data, such as a keypad 218 (hard or soft), a touch display, voice/speech or motion interfaces, scanners, readers, or other input device. In embodiments including a keypad 218, the keypad 218 can include (or cause display of) the conventional numeric (0-9) and related keys (#, *), and other keys used for operating the client computing device 101A and may include a full set of alphabetic keys or set of keys that may be activated to provide a full set of alphanumeric keys. In addition to providing input, the user input interface can be used, for example, to activate or deactivate certain functions, such as screen savers and/or sleep modes. Through such inputs the client computing device 101A can collect information/data, user interaction/input, and/or the like.

The client computing device 101A can also include volatile storage or memory 222 and/or non-volatile storage or memory 224, which can be embedded and/or may be removable. For example, the non-volatile memory may be ROM, PROM, EPROM, EEPROM, flash memory, MMCs, SD memory cards, Memory Sticks, CBRAM, PRAM, FeRAM, RRAM, SONOS, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. The volatile and non-volatile storage or memory can store databases, database instances, database management system entities, data, applications, programs, program modules, scripts, source code, object code, byte code, compiled code, interpreted code, machine code, executable instructions, and/or the like to implement the functions of the client computing device 101A-101N.

Figure 3:
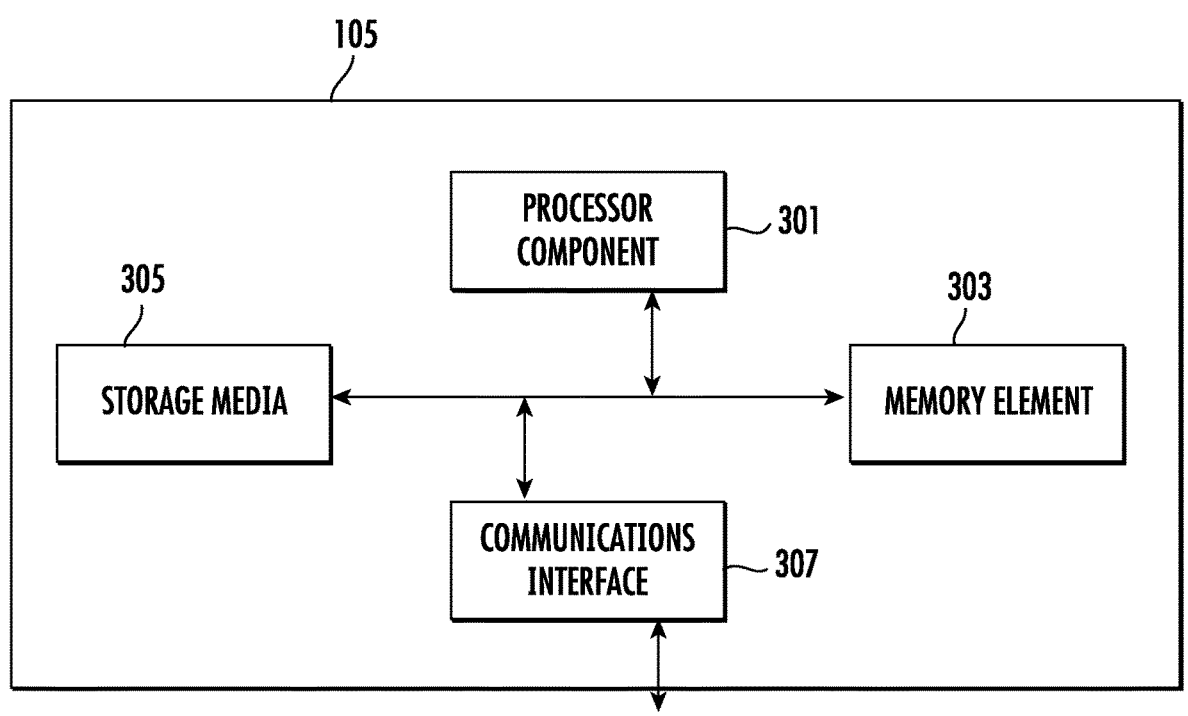
FIG. 3 illustrates an example schematic representation of an example remote computing server of an example remote computing platform in accordance with various embodiments of the present disclosure.

Referring now to FIG. 3, an example schematic representation of an example remote computing server 105 in an example remote computing platform in accordance with some example embodiments described herein. In some embodiments, the example remote computing platform may be a cloud computing platform, and the example remote computing server may be a cloud computing server.

As indicated, in some embodiments, the remote computing server 105 may include one or more network and/or communications interface 307 for communicating with various computing entities, such as by communicating data, content, information, and/or similar terms used herein that can be transmitted, received, operated on, processed, displayed, stored, and/or the like. For instance, the remote computing server 105 may communicate with controller component 107, one or more client computing devices 101A . . . 101N, and/or the like.

As shown in FIG. 3, in one embodiment, the remote computing server 105 may include or be in communication with one or more processor components (for example, processor component 301) (also referred to as processor components, processing circuitry, and/or similar terms used herein interchangeably) that communicate with other elements within the remote computing server 105 via a bus, for example, or network connection. As will be understood, the processor component 301 may be embodied in a number of different ways. For example, the processor component 301 may be embodied as one or more complex programmable logic devices (CPLDs), microprocessor components, multi-core processor components, co-processing entities, application-specific instruction-set processor components (ASIPs), and/or controllers. Further, the processor component 301 may be embodied as one or more other processing devices or circuitry. The term circuitry may refer to an entirely hardware embodiment or a combination of hardware and computer program products. Thus, the processor component 301 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processor component 301 may be configured for a particular use or configured to execute instructions stored in volatile or non-volatile media or otherwise accessible to the processor component 301. As such, whether configured by hardware or computer program products, or by a combination thereof, the processor component 301 may be capable of performing steps or operations according to embodiments of the present disclosure when configured accordingly.

In one embodiment, the remote computing server 105 may further include or be in communication with volatile media (also referred to as volatile storage, memory, memory storage, memory circuitry and/or similar terms used herein interchangeably). In one embodiment, the volatile storage or memory may also include one or more memory element 303 as described above, such as RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. As will be recognized, the volatile storage or memory element 303 may be used to store at least portions of the databases, database instances, database management system entities, data, applications, programs, program modules, scripts, source code, object code, byte code, compiled code, interpreted code, machine code, executable instructions, and/or the like being executed by, for example, the processor component 301 as shown in FIG. 3. Thus, the databases, database instances, database management system entities, data, applications, programs, program modules, scripts, source code, object code, byte code, compiled code, interpreted code, machine code, executable instructions, and/or the like may be used to control certain aspects of the operation of the remote computing server 105 with the assistance of the processor component 301 and operating system.

In one embodiment, the remote computing server 105 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or storage media 305 as described above, such as hard disks, ROM, PROM, EPROM, EEPROM, flash memory, MMCs, SD memory cards, Memory Sticks, CBRAM, PRAM, FeRAM, RRAM, SONOS, racetrack memory, and/or the like. As will be recognized, the non-volatile storage or storage media 305 may store databases, database instances, database management system entities, data, applications, programs, program modules, scripts, source code, object code, byte code, compiled code, interpreted code, machine code, executable instructions, and/or the like. The term database, database instance, database management system entity, and/or similar terms used herein interchangeably and in a general sense to refer to a structured or unstructured collection of information/data that is stored in a computer-readable storage medium.

Storage media 305 may also be embodied as a data storage device or devices, as a separate database server or servers, or as a combination of data storage devices and separate database servers. Further, in some embodiments, storage media 305 may be embodied as a distributed repository such that some of the stored information/data is stored centrally in a location within the system and other information/data is stored in one or more remote locations. Alternatively, in some embodiments, the distributed repository may be distributed over a plurality of remote storage locations only. An example of the embodiments contemplated herein would include a cloud data storage system maintained by a third-party provider and where some or all of the information/data required for the operation of the recovery prediction system may be stored.

As indicated, in one embodiment, the remote computing server 105 may also include one or more network and/or communications interface 307 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the remote computing server 105 may be configured to communicate via wireless external communication networks using any of a variety of protocols, such as general packet radio service (GPRS), Universal Mobile Telecommunications System (UMTS), Code Division Multiple Access 1900 (CDMA1900), CDMA1900 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), Institute of Electrical and Electronics Engineers (IEEE) 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol. The remote computing server 105 may use such protocols and standards to communicate using Border Gateway Protocol (BGP), Dynamic Host Configuration Protocol (DHCP), Domain Name System (DNS), File Transfer Protocol (FTP), Hypertext Transfer Protocol (HTTP), HTTP over TLS/SSL/Secure, Internet Message Access Protocol (IMAP), Network Time Protocol (NTP), Simple Mail Transfer Protocol (SMTP), Telnet, Transport Layer Security (TLS), Secure Sockets Layer (SSL), Internet Protocol (IP), Transmission Control Protocol (TCP), User Datagram Protocol (UDP), Datagram Congestion Control Protocol (DCCP), Stream Control Transmission Protocol (SCTP), HyperText Markup Language (HTML), and/or the like.

As will be appreciated, one or more of the remote computing server's components may be located remotely from components of other remote computing servers, such as in a distributed system. Furthermore, one or more of the components may be aggregated and additional components performing functions described herein may be included in the remote computing server 105. Thus, the remote computing server 105 can be adapted to accommodate a variety of needs and circumstances.

Figure 4:
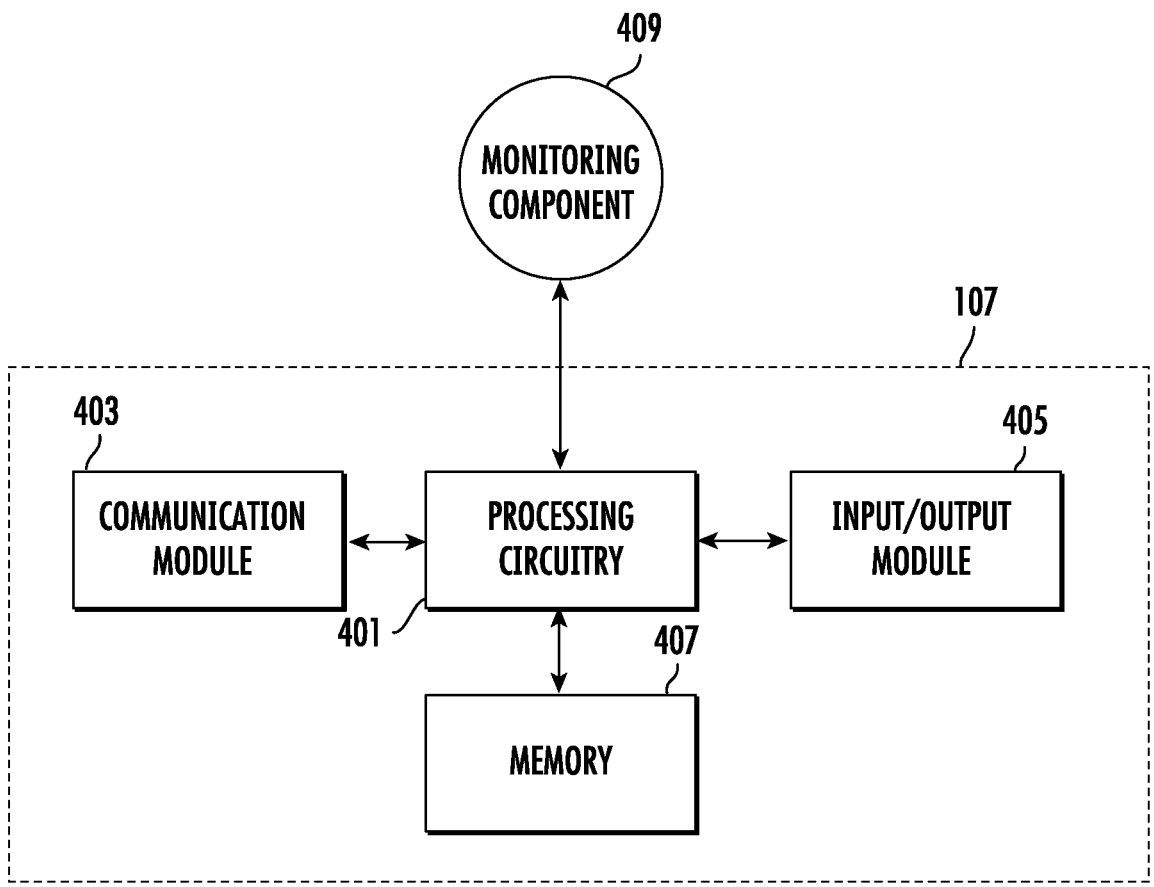
FIG. 4 illustrates an example schematic representation of an example controller component of an example IV monitoring device in accordance with various embodiments of the present disclosure.

Referring now to FIG. 4, a schematic diagram depicting an example controller component 107 of an example IV monitoring device in accordance with various embodiments of the present disclosure. As shown, the controller component 107 comprises processing circuitry 401, a communication module 403, input/output module 405, a memory 407 and/or other components configured to perform various operations, procedures, functions or the like described herein.

As shown, the controller component 107 (such as the processing circuitry 401, communication module 403, input/output module 405 and memory 407) is electrically coupled to and/or in electronic communication with a monitoring component 409. As depicted, the monitoring component 409 may exchange (e.g., transmit and receive) data with the processing circuitry 401 of the controller component 107. For example, monitoring component 409 may generate sensor data and transmit the sensor data to the processing circuitry 401.

The processing circuitry 401 may be implemented as, for example, various devices comprising one or a plurality of microprocessors with accompanying digital signal processors; one or a plurality of processors without accompanying digital signal processors; one or a plurality of coprocessors; one or a plurality of multi-core processors; one or a plurality of controllers; processing circuits; one or a plurality of computers; and various other processing elements (including integrated circuits, such as ASICs or FPGAs, or a certain combination thereof). In some embodiments, the processing circuitry 401 may comprise one or more processors. In one exemplary embodiment, the processing circuitry 401 is configured to execute instructions stored in the memory 407 or otherwise accessible by the processing circuitry 401. When executed by the processing circuitry 401, these instructions may enable the controller component 107 to execute one or a plurality of the functions as described herein. No matter whether it is configured by hardware, firmware/software methods, or a combination thereof, the processing circuitry 401 may comprise entities capable of executing operations according to the embodiments of the present invention when correspondingly configured. Therefore, for example, when the processing circuitry 401 is implemented as an ASIC, an FPGA, or the like, the processing circuitry 401 may comprise specially configured hardware for implementing one or a plurality of operations described herein. Alternatively, as another example, when the processing circuitry 401 is implemented as an actuator of instructions (such as those that may be stored in the memory 407), the instructions may specifically configure the processing circuitry 401 to execute one or a plurality of algorithms and operations described herein.

The memory 407 may comprise, for example, a volatile memory, a non-volatile memory, or a certain combination thereof. Although illustrated as a single memory in FIG. 4, the memory 407 may comprise a plurality of memory components. In various embodiments, the memory 407 may comprise, for example, a hard disk drive, a random-access memory, a cache memory, a flash memory, a Compact Disc Read-Only Memory (CD-ROM), a Digital Versatile Disk Read-Only Memory (DVD-ROM), an optical disk, a circuit configured to store information, or a certain combination thereof. The memory 407 may be configured to store information, data, application programs, instructions, and etc., so that the controller component 107 can execute various functions according to the embodiments of the present disclosure. For example, in at least some embodiments, the memory 407 is configured to cache input data for processing by the processing circuitry 401. Additionally, or alternatively, in at least some embodiments, the memory 407 is configured to store program instructions for execution by the processing circuitry 401. The memory 407 may store information in the form of static and/or dynamic information. When the functions are executed, the stored information may be stored and/or used by the controller component 107.

The communication module 403 may be implemented as any apparatus included in a circuit, hardware, a computer program product or a combination thereof, which is configured to receive and/or transmit data from/to another component or apparatus. The computer program product comprises computer-readable program instructions stored on a computer-readable medium (for example, the memory 407) and executed by a controller component 107 (for example, the processing circuitry 401). In some embodiments, the communication module 403 (as with other components discussed herein) may be at least partially implemented as the processing circuitry 401 or otherwise controlled by the processing circuitry 401. In this regard, the communication module 403 may communicate with the processing circuitry 401, for example, through a bus. The communication module 403 may comprise, for example, antennas, transmitters, receivers, transceivers, network interface cards and/or supporting hardware and/or firmware/software, and is used for establishing communication with another apparatus. The communication module 403 may be configured to receive and/or transmit any data that may be stored by the memory 407 by using any protocol that can be used for communication between apparatuses. The communication module 403 may additionally or alternatively communicate with the memory 407, the input/output module 405 and/or any other component of the controller component 107, for example, through a bus.

In some embodiments, the controller component 107 may comprise an input/output module 405. The input/output module 405 may communicate with the processing circuitry 401 to receive instructions input by the user and/or to provide audible, visual, mechanical or other outputs to the user. Therefore, the input/output module 405 may comprise supporting devices, such as a keyboard, a mouse, a display, a touch screen display, and/or other input/output mechanisms. Alternatively, at least some aspects of the input/output module 405 may be implemented on a device used by the user to communicate with the controller component 107. The input/output module 405 may communicate with the memory 407, the communication module 403 and/or any other component, for example, through a bus. One or a plurality of input/output modules and/or other components may be included in the controller component 107.

Figure 5:
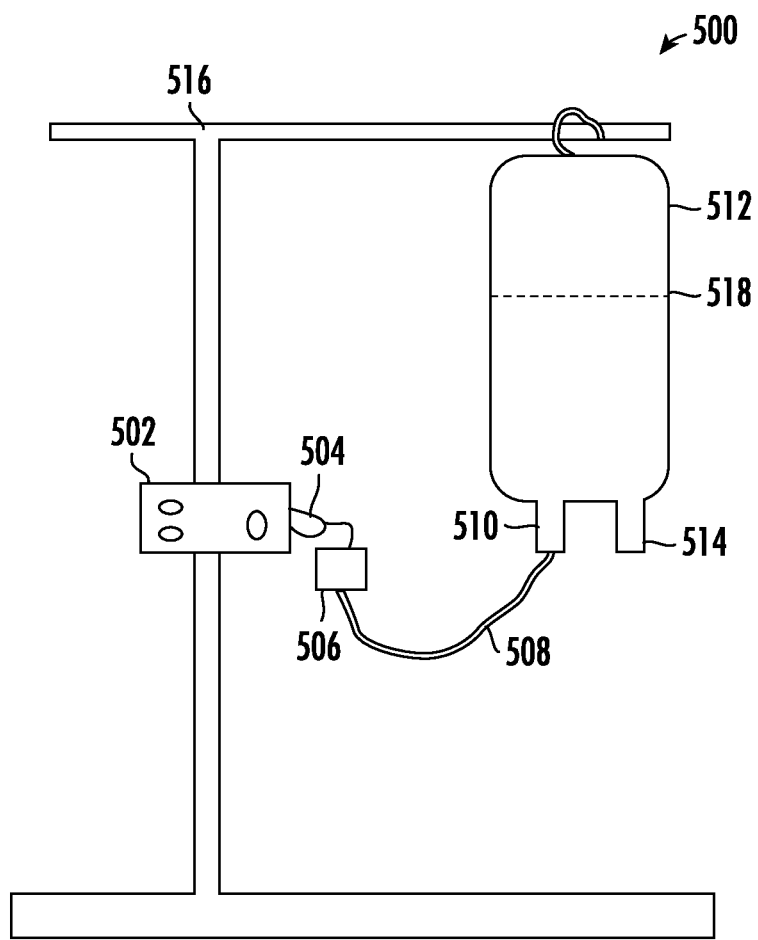
FIG. 5 illustrates an example schematic representation of an IV fluid bag monitoring system in accordance with various embodiments of the present disclosure.
Figure 6A:
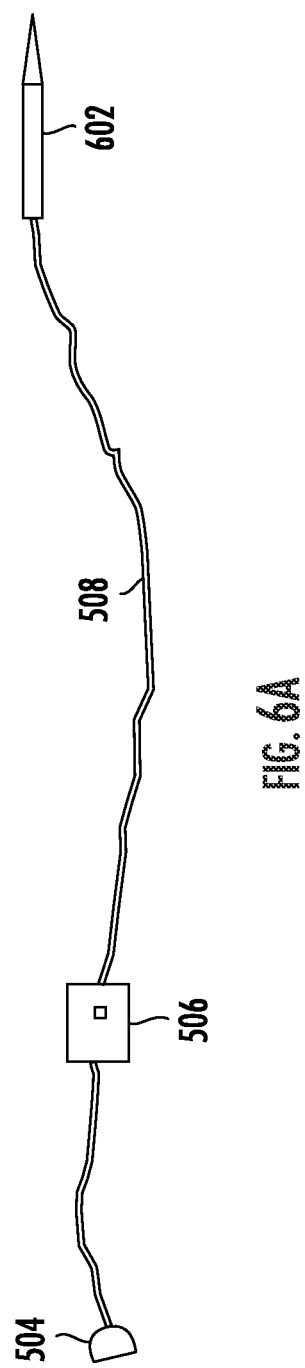
FIG. 6A and FIG. 6B illustrate exemplary replaceable components of an IV fluid bag monitoring system in accordance with various embodiments of the present disclosure.
Figure 6B:
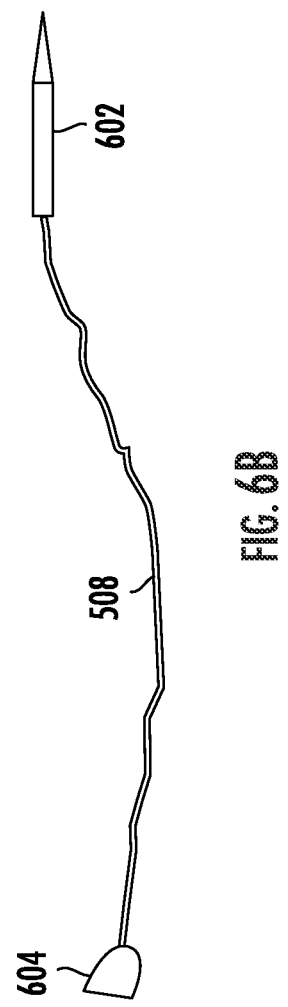

Referring now to FIG. 5, an IV fluid bag monitoring system is provided, which may be used in accordance with various embodiments of the present disclosure. In some embodiments, the IV fluid bag monitoring system 500 comprises controller component 502, electrical connector 504, sensor 506, IV tube 508, IV fluid bag 512, and stand 516. Sensor 506 may comprise a pressure sensor in a plastic enclosure including connections to the IV fluid bag 512 and the controller component 502. The connection to the IV fluid bag 512 comprises an IV tube 508 coupled to the sensor 506 at a first end of the IV tube 508. A second end of the IV tube 508 may include a cannula (e.g., cannula 602 as illustrated in FIGS. 6A and 6B) that is insertable into a fluid port 510 of the IV fluid bag 512. The connection to the controller component 502 comprises the electrical connector 504.

According to certain embodiments of the present disclosure, an assembly comprising electrical connector 504, sensor 506, and tube 508 may be provided as a replaceable unit, as shown in FIG. 6A. The assembly may be interchangeably coupled to controller component 502 via an electrical connection using electrical connector 504. According to another embodiment, the tube 508 may be provided as a replaceable unit, as shown in FIG. 6B. Tube 508 may be interchangeably coupled to sensor 506 with a fluid connector 604.

Referring back to FIG. 5, controller component 502 is configured on stand 516. According to various embodiments of the present disclosure, the controller component 502 is configured at a height such that the controller component 502 is level with the fluid port 510 to eliminate/minimize tube liquid pressure between sensor 506 and fluid port 510 from actual IV fluid bag hydrostatic pressure between IV fluid level 518 fluid port 510. This initial condition can be provided to controller component 502 by, for example, pressing a start button on controller component 502 to register initial pressure as start point. Upon connecting the IV tube 508 to fluid port 510 (e.g., via a cannula) IV tube 508 may be filled with a small quantity of IV fluid from IV fluid bag 512. The presence of IV fluid in in IV tube 508 may be detected by sensor 506.

Hydrostatic pressure at fluid port 510 and injection port 514 may result from a height difference between IV fluid level 518 and fluid port 510 or injection port 514. For example, hydrostatic pressure can be calculated by $P=\beta gh$, where '$\beta$' represents fluid density, g' represents gravitational constant, and 'h' represents the height difference. Hydrostatic pressure at fluid port 510 and injection port 514 may be equivalent or substantially similar. As such, sensor 506 may determine hydrostatic pressure of fluid from IV fluid bag 512 at injection port 514 by measuring hydrostatic pressure of fluid transmitted through IV tube 508 from IV fluid bag 512 at fluid port 510. As IV fluid is discharged at a set dosing rate to a patient via the infusion port 514, the IV fluid level 518 may decrease over time, hence pressure readings of sensor 506 can provide data corresponding to fluid level in real-time. The sensor 506 may have a measuring range of, for example, +/−60 mBar, that may correspond to a 61 cm height difference of IV fluid level 518 from height of controller component 502 (or fluid port 510).

Controller component 502 may comprise an intermediate communication aggregator (e.g., a gateway) to a central network or a remote server. The controller component 502 may perform interfacing with sensor 506 to retrieve hydrostatic pressures data values and process the data values to derive or calculate, remaining fluid volume, discharge rate, and any flow occlusion conditions associated with IV fluid bag 512. The controller component 502 may include a storage device to store the hydrostatic pressures data values and values calculated by the controller component 502 (e.g., remaining fluid volume, discharge rate, and any flow occlusion conditions). Any of the stored and calculated values may be transmitted by controller component 502 to RTHMS (e.g., remote computing server 105) as data load packages over a wired or wireless network. A data load package may include information, such as device tag number/identified, alert/alarm flags with time stamps and optionally configuration packet to set various control logic values as described in further detail below. The controller component 502 may also include physical buttons to initiate and stop monitoring of an IV fluid bag. The controller component 502 may further include visual/acoustic indicators to show respective alert and alarms with respect to monitoring characteristics (e.g., remaining fluid volume, discharge rate, and any flow occlusion conditions) of an IV fluid bag.

According to various embodiments of the present disclosure, RTHMS may comprise software framework hosted, e.g., on remote computing server 105, configured to receive data load packages as described above to process value added services in form of timely communique to nursing staff about alarms over mobile device dashboards, or provide monitoring information along with hospital enterprise level data visualization or analytics. A RTHMS may include an overall workflow controller that may provide nurse call, mobile dashboard, and enterprise rule engines to qualify alerts/alarms. In one embodiment, the RTHMS may manage a nurse call system in response to IV fluid bag related workflows.

FIG. 6A presents an exemplary replaceable component of an IV fluid bag monitoring system according to some embodiments of the present disclosure. Electrical connector 504, sensor 506, tube 508, and cannula 602 may be provided as a replaceable unit for coupling with controller component 502. The replaceable unit may be replaceable after each usage and may be interchangeably coupled to controller component 502 via an electrical connection using electrical connector 504. In certain embodiments, the tube 508 may be prefilled with saline to establish fluid pressure with sensor 506. Alternatively, as an economical solution, a replaceable unit comprising a fluid connector 604, tube 508, and cannula 602 may be interchangeably coupled to sensor 506. Fluid connector 604 may comprise a coupling for liquid applications, such as a Luer fluid connector. Upon connecting the cannula 602 to an IV fluid bag, fluid from the IV fluid bag may fill the tube 508 to establish fluid pressure with sensor 506 when fluid connector 604 is connected to sensor 506. As such, cost savings may be provided by keeping sensor 506 after each usage and discarding only connector 604, tube 508, and cannula 602.

Figure 7:
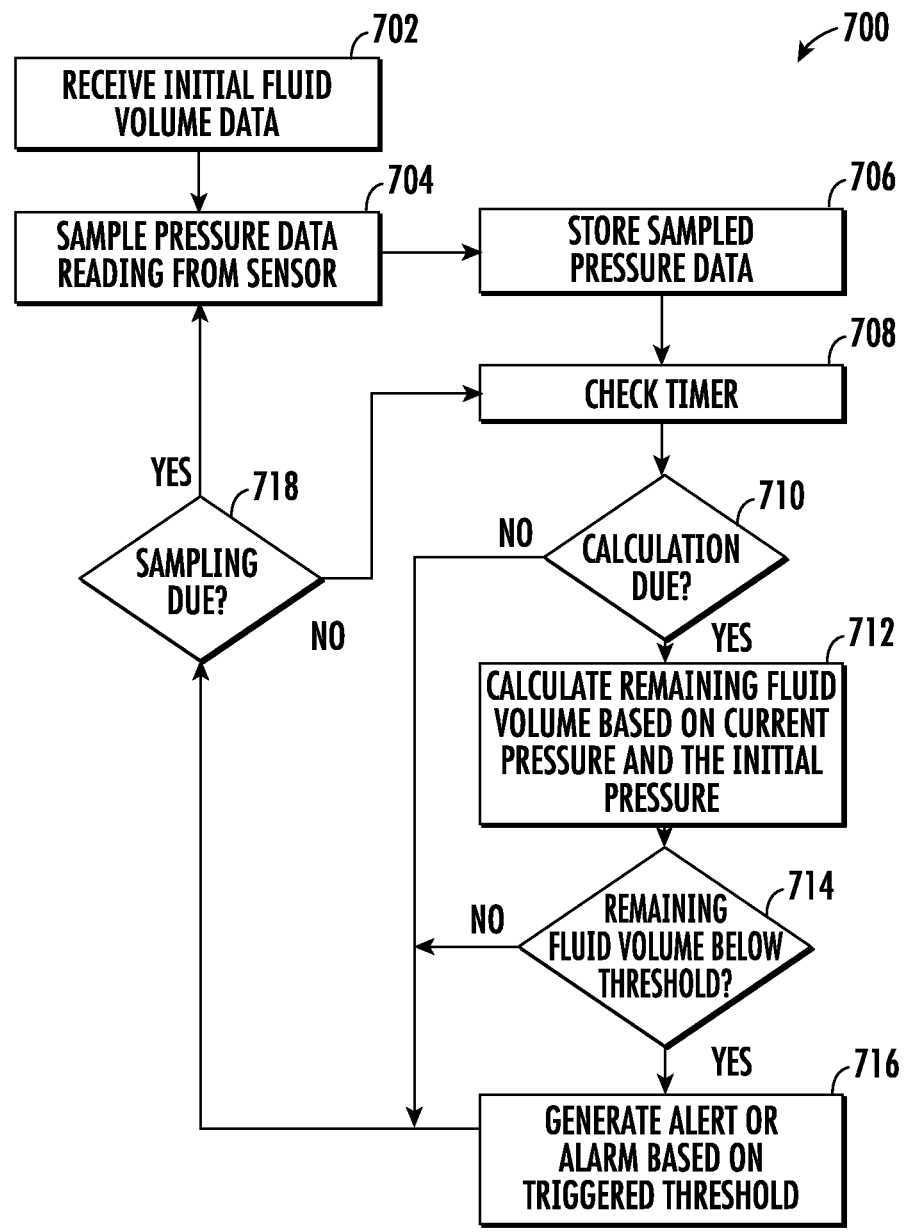
FIG. 7 illustrates an example flow diagram illustrating an example method for determining remaining fluid volume of an IV fluid bag in accordance with various embodiments of the present disclosure.
Figure 8:
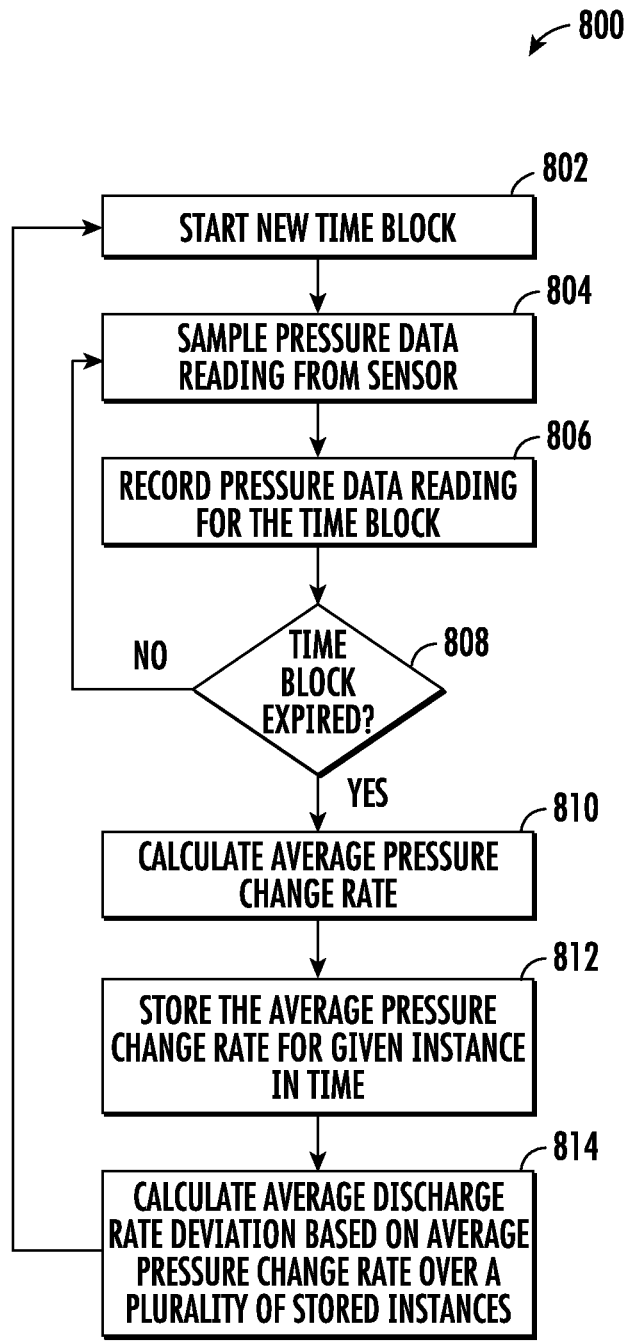
FIG. 8 illustrates an example flow diagram illustrating an example method for determining flow discharge rate in accordance with various embodiments of the present disclosure.
Figure 9:
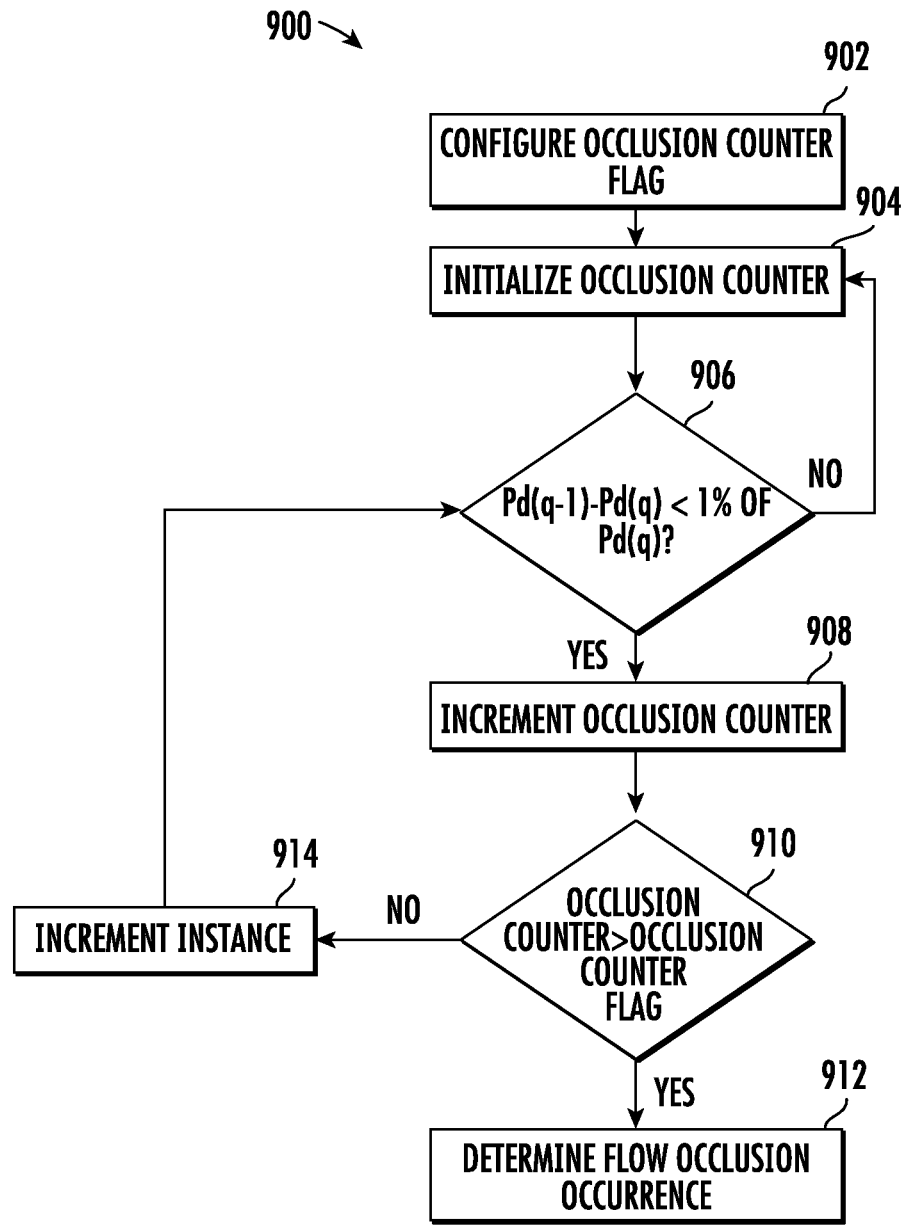
FIG. 9 illustrates an example flow diagram illustrating an example method for determining flow occlusion detection in accordance with various embodiments of the present disclosure.

Referring now to FIG. 7, FIG. 8, and FIG. 9, example flow diagrams illustrating exemplary methods of determining remaining fluid volume, fluid discharge rate, and flow occlusion by a controller component in accordance with some example embodiments of the present disclosure are provided. It is noted that each block of a flowchart, and combinations of blocks in the flowchart, may be implemented by various means such as hardware, firmware, circuitry and/or other devices associated with execution of software including one or more computer program instructions. For example, one or more of the steps/operations described in FIG. 7, FIG. 8, and FIG. 9 may be embodied by computer program instructions, which may be stored by a non-transitory memory of an apparatus employing an embodiment of the present disclosure and executed by a processor component in an apparatus (such as, but not limited to, a controller component, a programmable processor, a client computing device, a remote computing server, and/or the like). For example, these computer program instructions may direct the processor component to function in a particular manner, such that the instructions stored in the computer-readable storage memory produce an article of manufacture, the execution of which implements the function specified in the flowchart block(s).

As described above and as will be appreciated based on this disclosure, embodiments of the present disclosure may comprise various means including entirely of hardware or any combination of software and hardware. Furthermore, embodiments may take the form of a computer program product on at least one non-transitory computer-readable storage medium having computer-readable program instructions (e.g., computer software) embodied in the storage medium. Similarly, embodiments may take the form of a computer program code stored on at least one non-transitory computer-readable storage medium. Any suitable computer-readable storage medium may be utilized including non-transitory hard disks, CD-ROMs, flash memory, optical storage devices, or magnetic storage devices.

Referring now to FIG. 7, an example method 700 for determining remaining fluid volume of an IV fluid bag in accordance with some example embodiments described herein is illustrated. The example method 700 may be executed by a computing device associated with a controller component including processing circuitry and memory (for example, as illustrated and described above in connection with at least FIG. 4). At step 702, the controller component receives data representative of an initial fluid volume of an IV fluid bag. As an example, the controller component may include an interface (e.g., input/output model 405) for entering an initial fluid volume. The initial fluid volume may be used to calibrate calculation of remaining fluid volume. That is, the controller component may not directly measure actual volume contained in the IV fluid bag but instead approximates remaining fluid volume based on pressure data readings from a sensor coupled to the IV fluid bag.

In some embodiments, subsequent to step 702, the example method proceeds to step 704, where the controller component samples pressure data reading from a sensor coupled to the controller component. The sensor may comprise a pressure sensor configured to measure hydrostatic pressure at an injection port of an IV fluid bag.

In some embodiments, subsequent to step 704, the example method proceeds to step 706, where the controller component stores the sampled pressure data. In particular, the controller component may store at least values for an initial pressure and a current pressure.

In some embodiments, subsequent to step 706, the example method proceeds to step 708, where the controller component checks a timer. The timer may be used to determine sampling rate for pressure data readings and remaining fluid volume updates.

In some embodiments, subsequent to step 708, the example method proceeds to step 710, where the controller component determines whether a calculation of remaining fluid volume is due. The remaining fluid volume may be calculated at specific intervals, such as after every minute or as per user configuration and may be made available as part of a data load to be communicated to a RTHMS.

If an update is not due, the example method proceeds to step 718, where the controller component determines whether sampling of pressure data reading from the sensor is due. According to some embodiments, sampling rate of the sensor may be predetermined or programmable. For example, the sampling rate may be a reading every 20 seconds.

If sampling is due, the example method proceeds to step 704, where the controller component samples pressure data reading from the sensor. Otherwise, the example method proceeds to step 708, where the controller component checks the timer.

Returning back to step 710, in some embodiments, if calculation of remaining fluid volume is due, the example method proceeds to step 712, where the controller component calculates remaining fluid volume based on current pressure and the initial pressure. The controller component may also use the initial fluid volume data to calculate the remaining fluid volume. The remaining fluid volume may be used for displayed on a numerical display on the controller component and included as part of a data load to RTHMS.

The remaining fluid volume may be calculated in terms of percentage of volume left in the IV fluid bag. For example, remaining fluid volume may be calculated according to the following equation:

% volume left=(initial pressure−current pressure)/(initial pressure)*100.  Equation 1

In some embodiments, subsequent to step 712, the example method proceeds to step 714, where the controller component determines whether the remaining fluid volume is below a given threshold. Alert thresholds and alarm thresholds may be configured, for example, to suit response protocols. The alert thresholds and the alarm thresholds may be configured in terms of the remaining fluid volume. For example, an alert may be configured at 25% of remaining fluid volume while an alarm may be configured at 10% of remaining fluid volume. If the remaining fluid volume is not below the given threshold, the example method proceeds to step 718.

In some embodiments, subsequent to step 714, if the remaining fluid volume is below a given threshold, the example method proceeds to step 716, where the controller component generates an alert or alarm based on the remaining fluid volume being below the given threshold.

In some embodiments, subsequent to step 716, the example method proceeds to step 718, where the controller component determines whether sampling of pressure data reading from the sensor is due.

Referring now to FIG. 8, an example method 800 for determining flow discharge rate in accordance with some example embodiments described herein is illustrated. The example method 800 may be executed by a computing device associated with a controller component including processing circuitry and memory (for example, as illustrated and described above in connection with at least FIG. 4). At step 802, the controller component starts a new time block. The time block may be used to define a series of data points for calculating pressure change.

In some embodiments, subsequent to step 802, the example method proceeds to step 804, where the controller component samples pressure data reading from a sensor coupled to the controller component. The sensor may comprise a pressure sensor configured to measure hydrostatic pressure at an injection port of an IV fluid bag.

In some embodiments, subsequent to step 804, the example method proceeds to step 806, where the controller component records the pressure data reading for the time block.

In some embodiments, subsequent to step 806, the example method proceeds to step 808, where the controller component determines whether the time block has expired.

In some embodiments, subsequent to step 808, if the time block has not expired, the example method proceeds to step 804, wherein the controller component samples an additional pressure data reading from sensor. According to some embodiments, the controller component may sample pressure data reading from the sensor according to a given sampling rate. Steps 804 and 806 may be repeated by controller components until expiration of the time block.

In some embodiments, subsequent to step 808, if the time block has expired, the example method proceeds to step 810, where the controller component calculates average pressure change rate. The average pressure change rate may be calculated based on pressure data reading values over the given time block. For example, at a given sampling rate the average pressure change may be calculated using the following equation:

$$P_m = (p_1 + p_2 + \ldots + p_n)/n*tb \qquad \text{Equation 2}$$

In the above equation, $p_n$ represents pressure value at a given sampling over a configured time block 'tb' and 'm' represents the time block. The average pressure may correspond to relative IV fluid volume discharge.

In some embodiments, subsequent to step 810, the example method proceeds to step 812, where the controller component stores the average pressure change rate for a given instance. For example, a given time block may correspond to a given instance. Average pressure change rate $P_m$ may be stored for every 'q' instance.

In some embodiments, subsequent to step 812, the example method proceeds to step 814, where the controller component calculates average discharge rate deviation based on average pressure change rate over a plurality of stored instances. As an example, for 'q' instances, an average discharge rate deviation $P_d$ may be calculated using the following equation:

$$P_d = (P_{1,1} + P_{2,2} + \ldots + P_{m,q})/q \qquad \text{Equation 3}$$

In some embodiments, subsequent to step 814, the example method proceeds to step 802, wherein the controller component repeats the above-described steps. As such, the number of 'q' instances may increase over each iteration of example method 800 such that $P_d$ can be updated after each 'q'. The average discharge rate deviation may be included as part of a data load to RTHMS.

According to various embodiments of the present disclosure, the average discharge rate deviation may be used to generate flow discharge alerts and alarms. For example, a flow discharge alert may be configured based on FD_alert_value being +/−10%. A FD_alert_high may be generated based on whether a difference between an average discharge rate deviation of a prior instance $P_d(q-1)$ and an average discharge rate deviation of a current instance $P_d(q)$ is greater than FD_alert_value of the average discharge rate deviation of the prior instance Pd(q−1). If the difference is less than FD_alert_value, a FD_alert_low may be generated. A flow discharge alert may comprise setting a corresponding flag in a data load transmitted to the RTHMS and/or causing a visual and/or audio indication on the controller component.

Similarly, a flow discharge alarm may be configured based on FD_alarm_value being +/−5%. A FD_alarm_high may be generated if a difference between an average discharge rate deviation of a prior instance $P_d(q-1)$ and an average discharge rate deviation of a current instance $P_d(q)$ is greater than FD_alarm_value of the average discharge rate deviation of the prior instance $P_d(q-1)$. If the difference is less than FD_alarm_value, a FD_alarm_low may be generated. A flow discharge alarm may comprise setting a corresponding flag in a data load transmitted to the RTHMS and/or causing a visual and/or audio indication on the controller component.

Referring now to FIG. 9, an example method 900 for determining flow occlusion detection in accordance with some example embodiments described herein is illustrated. The example method 900 may be executed by a computing device associated with a controller component including processing circuitry and memory (for example, as illustrated and described above in connection with at least FIG. 4). According to embodiments of the present disclosure flow occlusion may comprise flow stoppage from an IV fluid bag due to tube kink, bend, or other obstruction preventing distribution of IV fluid from the IV fluid bag.

At step 902, the controller component configures an occlusion counter flag. For example, an OC_flag may be set to a value of '20' representative of a total time lapse where there is stagnate of pressure change due to IV fluid discharge occluded.

In some embodiments, subsequent to step 902, the example method proceeds to step 904, where the controller component initializes an occlusion counter. The occlusion counter may be configured to count the number of successive flow occlusion events (e.g., a decrease in average discharge rate deviation below a certain threshold) over a plurality of instances which is described in further detail with respect to the description of step 906.

In some embodiments, subsequent to step 904, the example method proceeds to step 906, where the controller component determines whether the difference between an average discharge rate deviation of a prior instance $P_d(q-1)$ and an average discharge rate deviation of a current instance $P_d(q)$ is less than 1% of the average discharge rate deviation of the current instance $P_d(q)$. If the difference is not less than 1%, the example method 900 proceeds to step 904 wherein the controller component resets the occlusion counter.

In some embodiments, subsequent to step 906, if the difference is less than 1%, the example method proceeds to step 908, where the controller component increments the occlusion counter.

In some embodiments, subsequent to step 908, the example method proceeds to step 910, where the controller component determines whether the occlusion counter is greater than the occlusion counter flag. That is, the controller component determines whether the number of successive flow occlusion events is greater than a value of the occlusion counter flag. In some embodiments, subsequent to step 910, if the occlusion counter is not greater than the occlusion counter flag, the example method proceeds to step 914, where the controller component increments the instance. Incrementing the next instance may comprise examining a next instance for examining average discharge rate deviation. In some embodiments, subsequent to step 914, the example method proceeds to step 906.

In some embodiments, subsequent to step 910, if the occlusion counter is greater than the occlusion counter flag, the example method proceeds to step 912, where the controller component determines the occurrence of a flow occlusion. Determining the occurrence of a flow occlusion may include setting a corresponding flag in a data load transmitted to the RTHMS and/or causing a visual and/or audio indication on the controller component.

As described above and as will be appreciated based on this disclosure, embodiments of the present disclosure may comprise various means including entirely of hardware or any combination of software and hardware. Furthermore, embodiments may take the form of a computer program product on at least one non-transitory computer-readable storage medium having computer-readable program instructions (e.g., computer software) embodied in the storage medium. Similarly, embodiments may take the form of a computer program code stored on at least one non-transitory computer-readable storage medium. Any suitable computer-readable storage medium may be utilized including non-transitory hard disks, CD-ROMs, flash memory, optical storage devices, or magnetic storage devices.

It is to be understood that the disclosure is not to be limited to the specific embodiments disclosed, and that modifications and other embodiments are intended to be included within the scope of the appended claims. Although specific terms are employed herein, they are used in a generic and descriptive sense only and not for purposes of limitation, unless described otherwise.

What is claimed is:

1. An intravenous (IV) fluid bag monitoring system comprising:
   a replaceable unit comprising:
      a sensor comprising a pressure sensor configured to measure hydrostatic pressure;
      an electrical connector coupling the sensor to a controller component;
      a cannula configurable for insertion into a fluid port of an IV fluid bag; and
      an IV tube coupling the sensor to an IV fluid bag via the cannula; and
   the controller component configured to:
      retrieve data representative of hydrostatic pressure from the sensor; and
      calculate remaining fluid volume, discharge rate, and flow occlusion based on the retrieved data.

2. The IV fluid bag monitoring system of claim 1 wherein the controller component is further configured to transmit data load packages to a remote computing server, the data load packages including the retrieved data and the calculated remaining fluid volume, discharge rate, and flow occlusion.

3. The IV fluid bag monitoring system of claim 1 wherein the controller component further includes visual and acoustic indicators that show respective alert and alarms with respect to the calculated remaining fluid, discharge rate, and flow occlusion.

4. The IV fluid bag monitoring system of claim 1 wherein the controller component is configured on a stand at a height that is level with the fluid port.

5. The IV fluid bag monitoring system of claim 1 wherein the sensor is configured to measure hydrostatic pressure of fluid transmitted through the IV tube from the IV fluid bag at the fluid port.

6. The IV fluid bag monitoring system of claim 1 wherein the controller component is further configured to:
   store at least values for an initial pressure and a current pressure; and
   calculate remaining fluid volume based on the current pressure and the initial pressure.

7. The IV fluid bag monitoring system of claim 1 wherein the controller component is further configured to:
   determine the remaining fluid volume is below a given threshold; and
   generate an alert or alarm based on the remaining fluid volume being below the given threshold.

8. The IV fluid bag monitoring system of claim 1 wherein the controller component is further configured to:
   calculate average pressure change rate based on pressure data reading values over a plurality of time blocks;
   for each of the plurality of time blocks, store an average pressure change rate as an instance; and
   calculate average discharge rate deviation based on average pressure change rate over a plurality of stored instances.

9. The IV fluid bag monitoring system of claim 1 wherein the controller component is further configured to: generate flow discharge alerts and alarms based on a difference between an average discharge rate deviation of a prior instance and an average discharge rate deviation of a current instance being greater than or less than a threshold value of the average discharge rate deviation of the prior instance.

10. The IV fluid bag monitoring system of claim 1 wherein the controller component is further configured to: count a number of successive flow occlusion events.

11. The IV fluid bag monitoring system of claim 10 wherein the flow occlusion events include a decrease in average discharge rate deviation below a given threshold.

12. The IV fluid bag monitoring system of claim 10 wherein the controller component is further configured to: determine whether a difference between an average discharge rate deviation of a prior instance and an average discharge rate deviation of a current instance is less than 1% of the average discharge rate deviation of the current instance.

13. The IV fluid bag monitoring system of claim 10 wherein the controller component is further configured to: determine the number of successive flow occlusion events is greater than an occlusion counter flag.

14. An intravenous (IV) fluid bag monitoring system comprising:
   a sensor comprising a pressure sensor configured to measure hydrostatic pressure;
   a replaceable unit comprising:
      a cannula configurable for insertion into a fluid port of an IV fluid bag;
      an IV tube coupling the sensor to an IV fluid bag via the cannula; and
      a fluid connector coupling the IV tube to the sensor;
   an electrical connector coupling the sensor to a controller component; and
   the controller component configured to:
   retrieve data representative of hydrostatic pressure from the sensor; and
   calculate remaining fluid volume, discharge rate, and flow occlusion based on the retrieved data.

15. The IV fluid bag monitoring system of claim 14 wherein the sensor is configured to measure hydrostatic pressure of fluid transmitted through the IV tube from the IV fluid bag at the fluid port.

16. The IV fluid bag monitoring system of claim 14 wherein the controller component is further configured to:
   store at least values for an initial pressure and a current pressure; and
   calculate remaining fluid volume based on the current pressure and the initial pressure.

17. The IV fluid bag monitoring system of claim 14 wherein the controller component is further configured to:
   determine the remaining fluid volume is below a given threshold; and
   generate an alert or alarm based on the remaining fluid volume being below the given threshold.

18. The IV fluid bag monitoring system of claim 14 wherein the controller component is further configured to:
   calculate average pressure change rate based on pressure data reading values over a plurality of time blocks;
   for each of the plurality of time blocks, store an average pressure change rate as an instance; and
   calculate average discharge rate deviation based on average pressure change rate over a plurality of stored instances.

19. The IV fluid bag monitoring system of claim 14 wherein the controller component is further configured to: generate flow discharge alerts and alarms based on a difference between an average discharge rate deviation of a prior instance and an average discharge rate deviation of a current instance being greater than or less than a threshold value of the average discharge rate deviation of the prior instance.

20. The IV fluid bag monitoring system of claim 14 wherein the controller component is further configured to: count a number of successive flow occlusion events.

* * * * *